United States Patent
Schuchardt et al.

(10) Patent No.: US 10,456,230 B2
(45) Date of Patent: Oct. 29, 2019

(54) METHOD OF FIXING SURGICAL SUTURE TO TISSUE

(71) Applicant: Coloplast A/S, Humlebaek (DK)

(72) Inventors: Sarah J. Schuchardt, Minneapolis, MN (US); Michael M. Witzmann, Shoreview, MN (US)

(73) Assignee: Coloplast A/S, Humlebaek (DK)

( * ) Notice: Subject to any disclaimer, the term of this patent is extended or adjusted under 35 U.S.C. 154(b) by 146 days.

(21) Appl. No.: 15/347,829

(22) Filed: Nov. 10, 2016

(65) Prior Publication Data

US 2017/0086957 A1 Mar. 30, 2017

Related U.S. Application Data

(63) Continuation of application No. 14/074,731, filed on Nov. 8, 2013, now Pat. No. 9,522,000.

(51) Int. Cl.
*A61F 2/00* (2006.01)
*A61B 17/04* (2006.01)
*A61B 17/00* (2006.01)

(52) U.S. Cl.
CPC ........ *A61F 2/0045* (2013.01); *A61B 17/0401* (2013.01); *A61B 17/0487* (2013.01); *A61B 2017/00438* (2013.01); *A61B 2017/0403* (2013.01); *A61B 2017/0404* (2013.01); *A61B 2017/0409* (2013.01); *A61B 2017/0414* (2013.01); *A61B 2017/0437* (2013.01); *A61B 2017/0464* (2013.01)

(58) Field of Classification Search
CPC ........ A61B 17/0401; A61B 2017/0409; A61B 2017/0414; A61B 2017/0488
See application file for complete search history.

(56) References Cited

U.S. PATENT DOCUMENTS

| | | | | |
|---|---|---|---|---|
| 2004/0243178 | A1* | 12/2004 | Haut | A61B 17/0401 606/232 |
| 2009/0259260 | A1* | 10/2009 | Bentley | A61B 17/0057 606/300 |
| 2010/0036395 | A1* | 2/2010 | Miller | A61B 17/0401 606/139 |
| 2010/0130989 | A1* | 5/2010 | Bourque | A61B 17/0401 606/144 |
| 2011/0202074 | A1* | 8/2011 | Talmo | A61B 17/0401 606/145 |
| 2014/0179991 | A1* | 6/2014 | Miller | A61F 2/0045 600/37 |

* cited by examiner

*Primary Examiner* — Thomas M McEvoy
(74) *Attorney, Agent, or Firm* — Coloplast Corp., Coloplast A/S; Nick Baumann

(57) ABSTRACT

A method of fixing surgical suture to tissue includes loading an anchor into a delivery guide and locating a fixation device outside of the delivery guide, with the anchor and the fixation device attached by a suture. The method includes providing an anchor deployment component coupled with the delivery guide and located proximal to the anchor, with a spring mechanism located between a distal portion of the anchor deployment component and the anchor. The method includes moving the anchor deployment component in a distal direction through the delivery guide, pushing the anchor out of the delivery guide, and delivering the anchor into tissue.

16 Claims, 14 Drawing Sheets

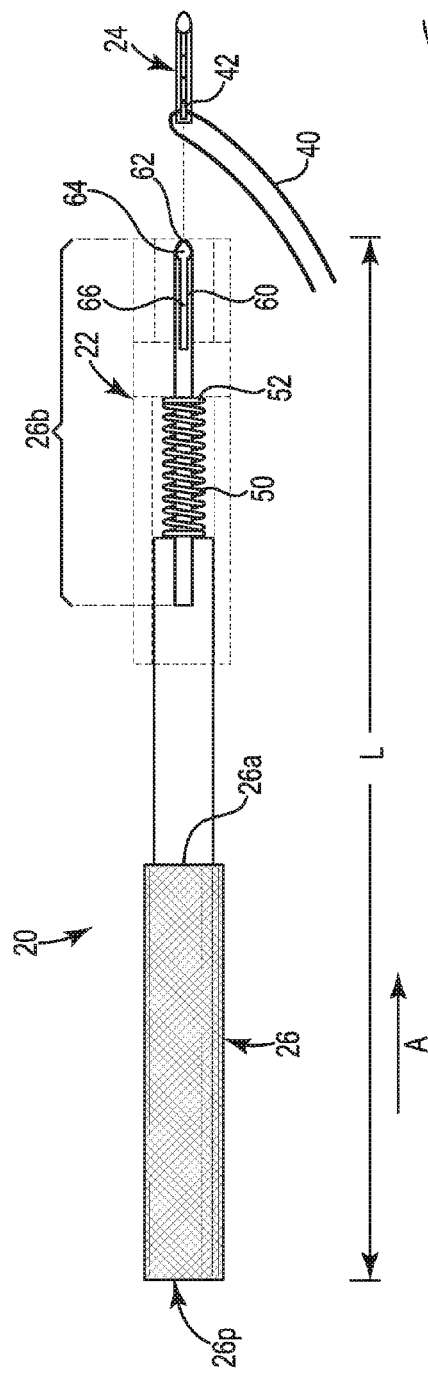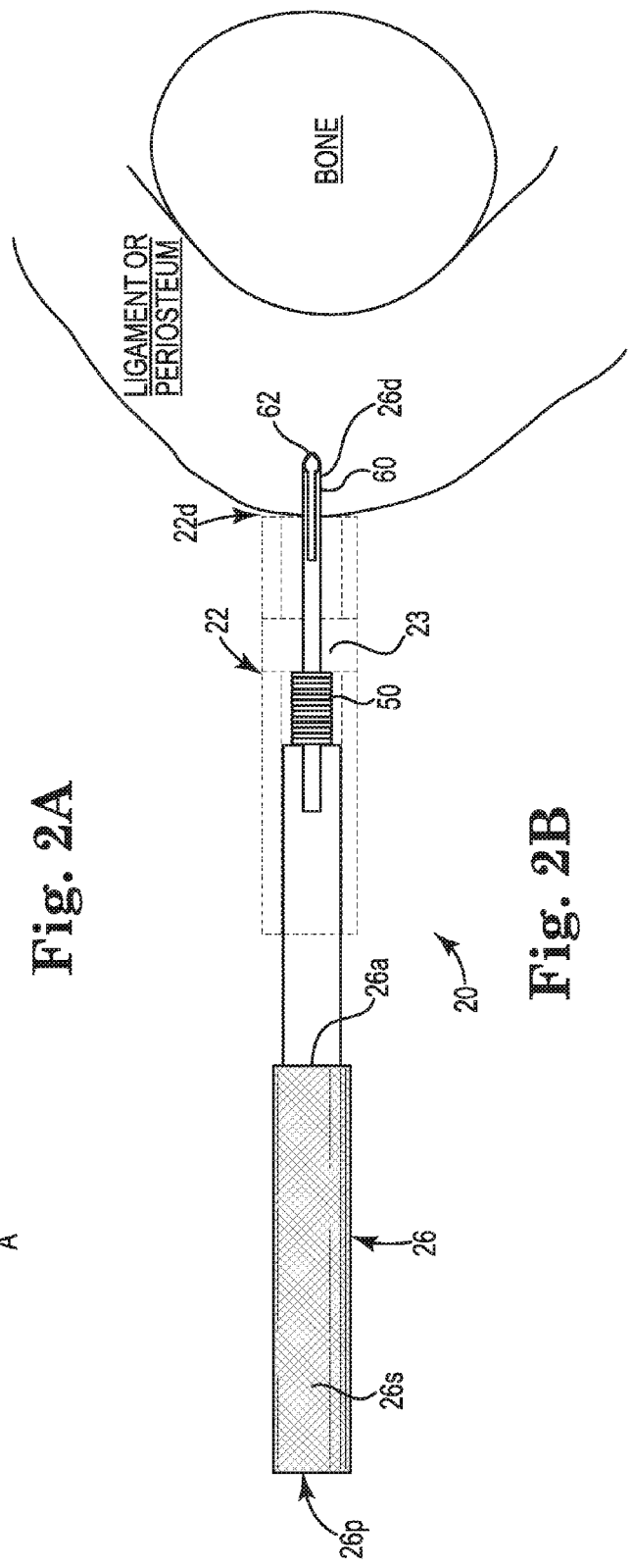

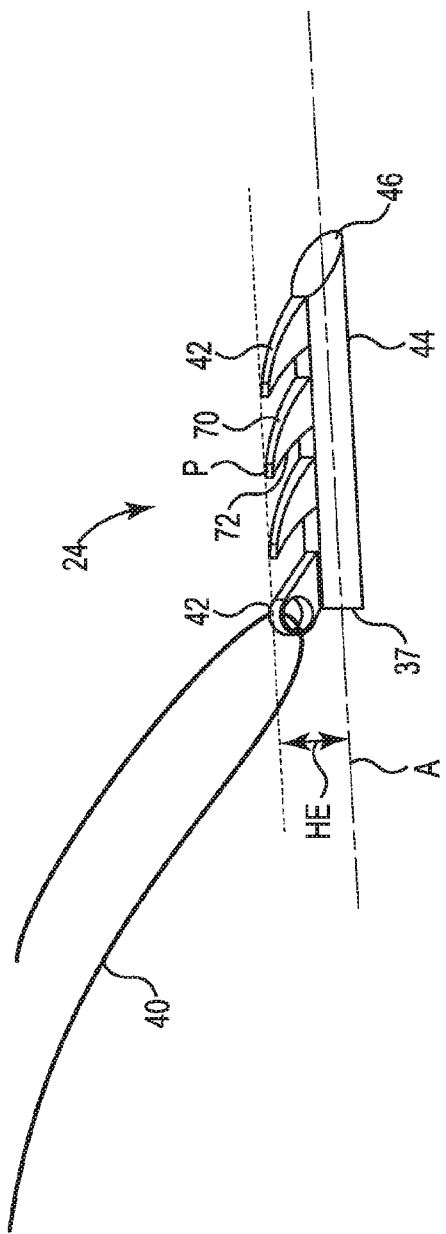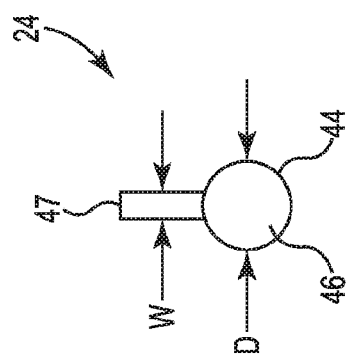
Fig. 3A
Fig. 3B

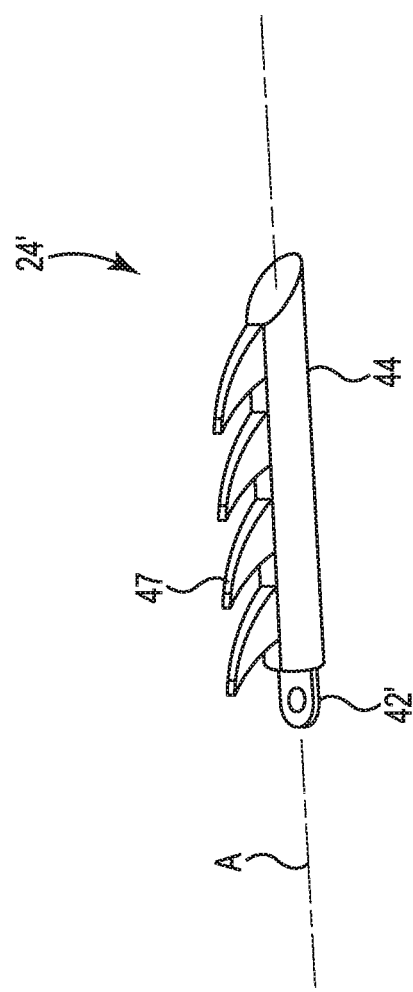

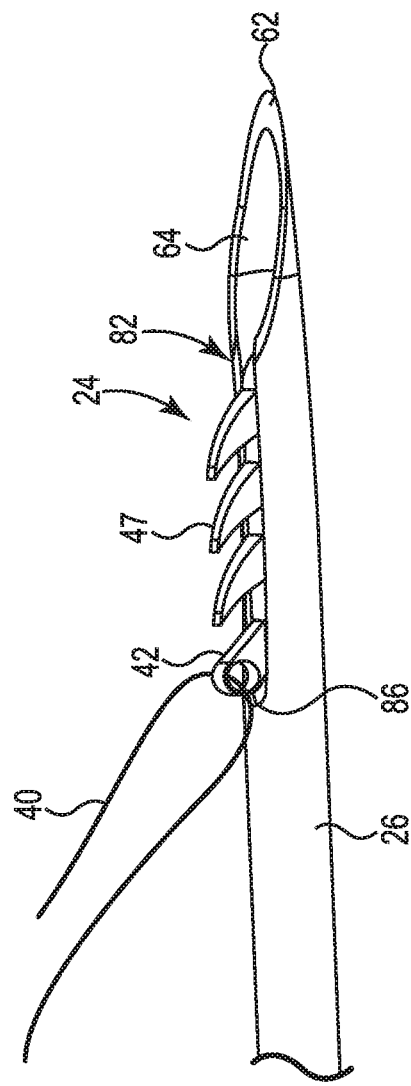

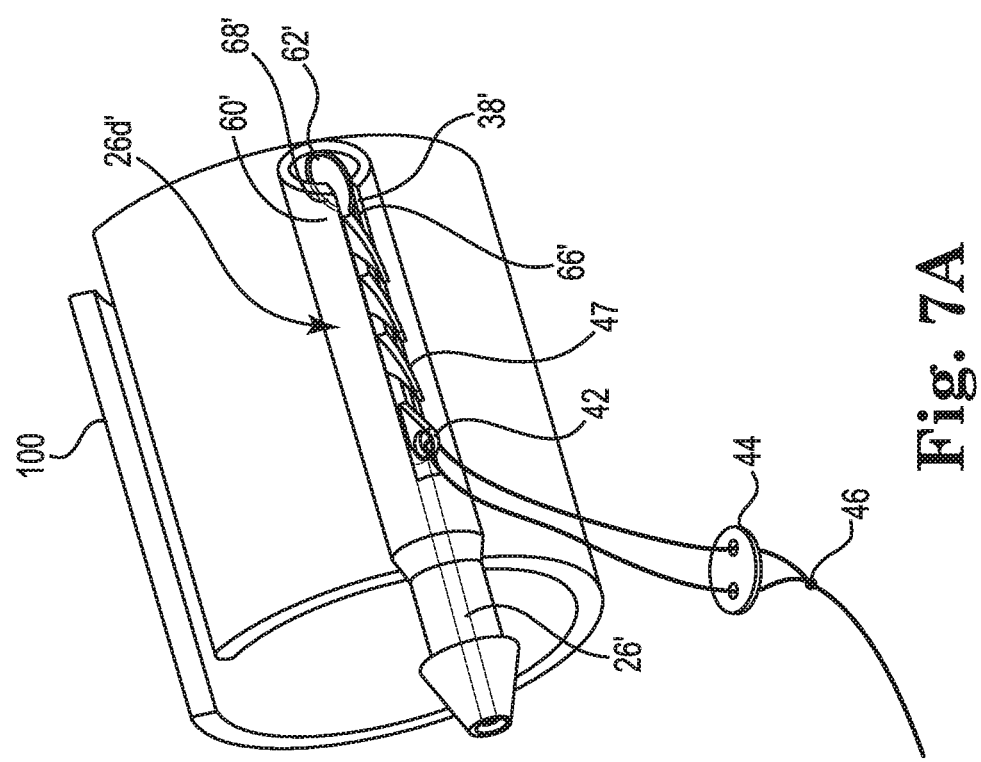

METHOD OF FIXING SURGICAL SUTURE TO TISSUE

BACKGROUND

Intracorporeal suturing of tissue during surgery presents challenges to the surgeon in that the surgeon is called upon to manipulate suturing instruments within the confines of a relatively small incision formed in the patient's body. In some cases, the surgeon is unable to see the suture site. In such a case, the surgeon will digitally palpate with a finger to locate a landmark within the intracorporeal site, and then deliver the suture at or near the landmark. Tying of the suture inside the patient at the intracorporeal site can be challenging since the surgeon is unable to see the site.

Improved suturing instruments and improved methods of delivering sutures would be welcomed by the surgical staff.

SUMMARY

One aspect provides a surgical suture fixation system that includes a delivery guide, an anchor, a movable anchor deployment component and a spring mechanism provided between the delivery guide and the anchor deployment component. The delivery guide includes a conduit that guides the anchor deployment component. The conduit has a channel formed through at least a part of its sidewall. The anchor has a length of suture including a fixation device (or engagement slider) attached to it. The length of suture extends through the channel in the delivery and the fixation device is provided externally of the delivery guide. The anchor deployment component is configured to receive the anchor and to deliver the anchor into a tissue location. The system is adapted to fixing the suture to a tissue location with the anchor for supporting an implantable support material in a patient.

One aspect provides a method of fixing surgical suture to tissue. The method includes loading an anchor having a length of suture attached thereto in an anchor deployment component. The method includes identifying a tissue location on the sacrospinous ligament, the arcus tendenius ligament or the periosteum covering the pubic bone with a finger. The method includes locating a delivery guide associated with the anchor deployment component alongside the finger. The method includes delivering the anchor into the tissue location by moving the anchor deployment component through the delivery guide in a distal direction. The method includes compressing a spring between the delivery guide and the anchor deployment component.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other. Like reference numerals designate corresponding similar parts.

FIG. 2A is a schematic side view of one embodiment of a surgical suture fixation system.

FIG. 2B is a schematic side view of one embodiment of a surgical suture fixation system.

FIG. 3A is a perspective view of one embodiment of the anchor illustrated in FIG. 1A.

FIG. 3B is an end view of the anchor.

FIG. 3C is a perspective view of one embodiment of an anchor.

FIG. 5 is a perspective view of the anchor inserted into a lumen of the anchor deployment component illustrated in FIG. 4.

FIG. 7A is a perspective view of one embodiment of a surgical suture fixation system including a finger housing and a cannula.

DETAILED DESCRIPTION

Figure 1A:
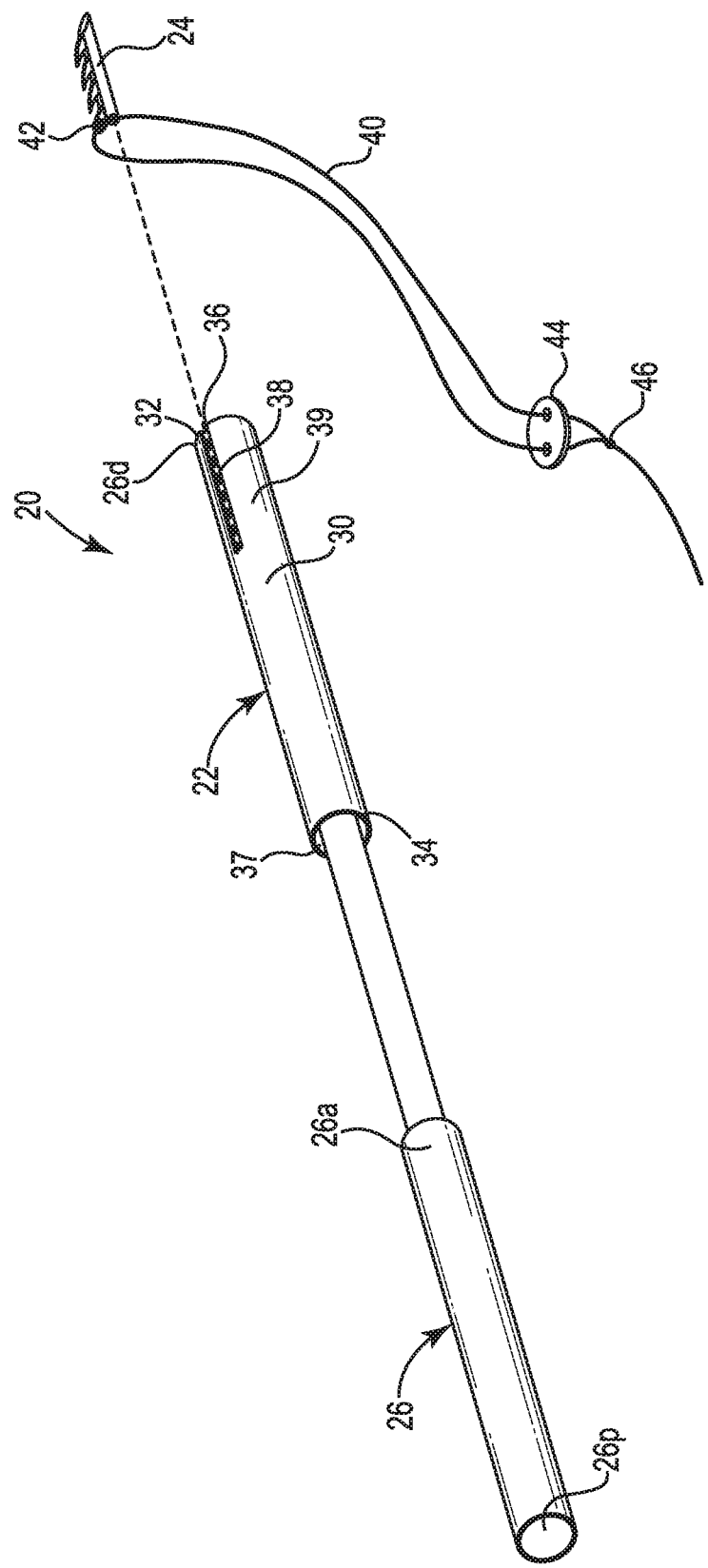
FIG. 1A is a perspective view of one embodiment of a surgical suture fixation system including an anchor that is insertable into an anchor deployment component.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

It is to be understood that the features of the various exemplary embodiments described herein may be combined with each other, unless specifically noted otherwise.

Tissue includes soft tissue, which includes dermal tissue, sub-dermal tissue, ligaments, tendons, or membranes. As employed in this specification, the term "tissue" does not include bone.

The descriptors "proximal" and "distal" are taken relative to the surgeon using the instrument. Thus, a distal direction is towards the tissue of the patient and a proximal direction is towards the surgeon and away from the tissue of the patient. A distal end is the furthest endmost location of a distal portion of a thing being described, whereas a proximal end is the nearest endmost location of a proximal portion of the thing being described.

Embodiments provide a surgical suture fixation system including an anchor deployment component useful to deliver an anchor to a tissue location inside the body of a patient. The anchor deployment component is guided through a conduit of a delivery guide. At a first end, the anchor deployment component includes a cannula that allows placement of an anchor at a tissue location deep within an incision site, which may be out of the field of vision of the surgeon. At a second opposite end provided outside the patient's body, the anchor deployment component includes a handle. The system is provided with a spring between the anchor deployment component and the delivery guide. When the second end of the anchor deployment component is pushed towards a tissue location in the patient's body, the spring compresses to a loaded configuration while the cannula moves through the conduit and into the tissue to deliver the anchor. When the spring is released from its loaded state, the cannula ejects from the tissue location leaving the anchor in the desired place. The system has a length of suture that is attached to the anchor and a fixation device attached to the suture. The suture extends exterior to the patient and the fixation device extends outside of the anchor deployment component and delivery guide. The suture is available to allow the surgeon to deliver a support along the suture from outside of the patient to the anchor location inside the patient. The fixation device slides along the suture to fix the support at or near the anchor location inside the patient.

Figure 1B:
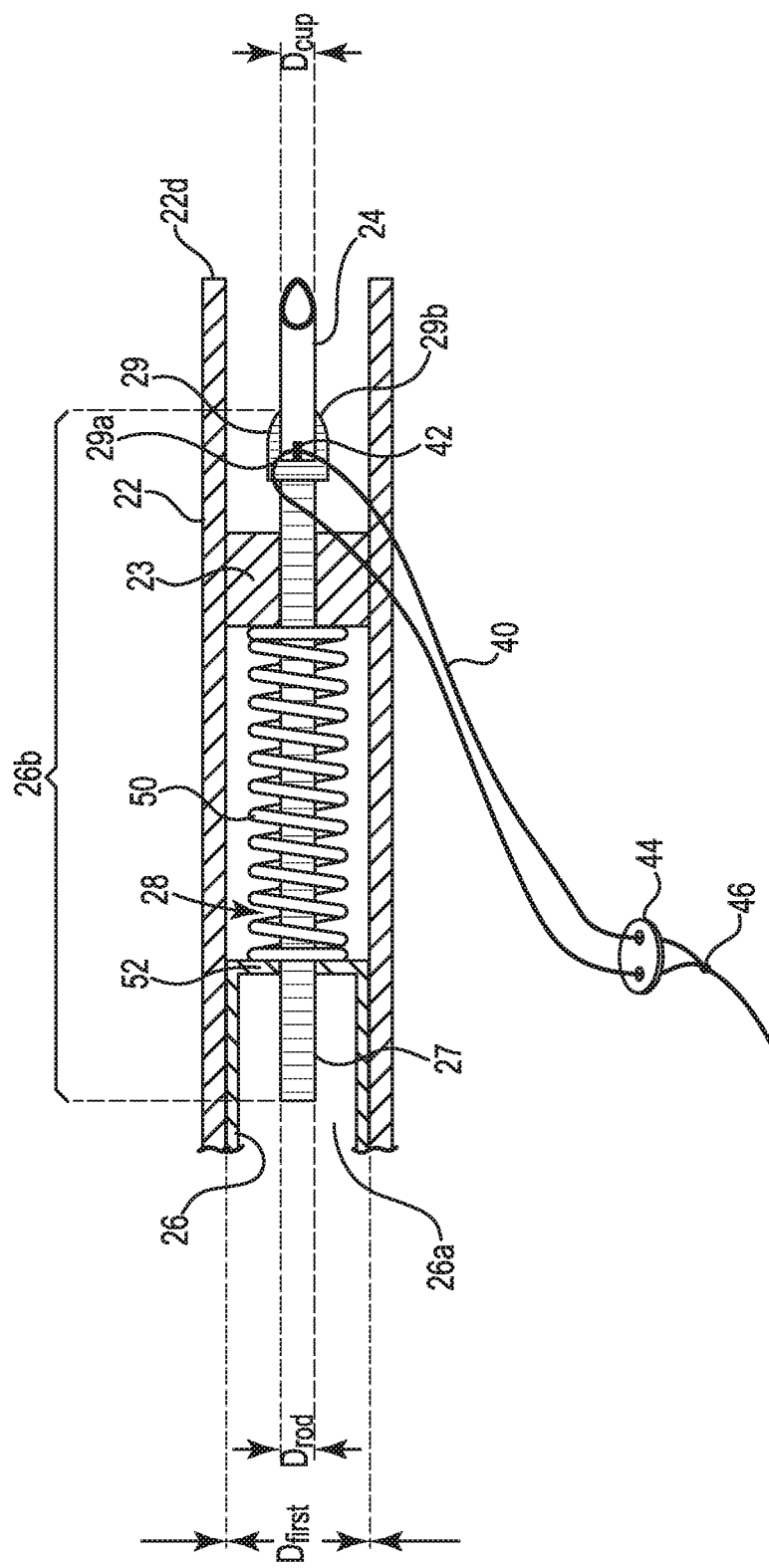
FIG. 1B is a schematic partial cross-sectional view of the surgical suture fixation system illustrated in FIG. 1A.

FIGS. 1A is a perspective view and FIG. 1B is a cross-sectional view of one embodiment of a surgical suture fixation system 20 including a delivery guide 22, an anchor 24, a movable anchor deployment mechanism 26 and a spring mechanism 28 (FIG. 1B).

The delivery guide 22 includes a conduit 30 having a distal end 32 and a proximal end 34. The conduit 30 of the delivery guide 22 includes an opening 36 in the distal end 32, an opening or passage 37 in the proximal end 34, and a channel 38 formed through the thickness of a sidewall 39. The channel 38 extends from the distal end 32 of the conduit 30 partway to the proximal end 34 of the conduit 30. In one embodiment, the channel 38 extends the entire distance between the distal end 32 and the proximal end 34 of the conduit 30. In one embodiment, the openings 36 and 37 in the distal and proximal ends 32 and 34, respectively, are sized to provide passage for the movable anchor deployment component 26 to move proximally and distally through the openings 36, 37.

In one embodiment, the anchor 24 has a length of suture 40 attached to it through an eyelet 42 provided on the anchor 24. The anchor 24 is received by the movable anchor deployment component 26 located in the conduit 30 of the delivery guide 22 to be in a position ready for insertion into tissue. In FIG. 1A, the length of suture 40 is shown exiting through the channel 38 of the delivery guide 22. In one embodiment, the length of suture 40 includes an engagement slider 44 and a slip knot 46. FIG. 1A illustrates an anchor 24 shown outside of the anchor deployment component 26 and the delivery guide 22, at the end of a phantom line extending from the distal end 32 of the conduit 30 of the delivery guide 22. Also shown in phantom line is the length of suture 40 attached to the anchor 24 through eyelet 42.

The movable anchor deployment component 26 includes a proximal portion having a proximal end 26p and a distal portion having a distal end 26d. The anchor deployment component 26 defines a longitudinal extent "L" (FIG. 2A) between its proximal and distal ends 26p, 26d. In one embodiment, the proximal portion of the anchor deployment component 26 includes a first body section 26a and the distal portion includes a second body section 26b (FIG. 1B). The first body section 26a extends from the proximal end 26p into engagement with the delivery guide 22. The second body section 26b is associated with the first body section 26a at a position lying inside the conduit 30 of the delivery guide 22.

FIG. 1B is a cross-sectional view of a distal portion of the surgical suture fixation system 20. FIG. 1B illustrates one embodiment wherein the second body section 26b of the movable anchor deployment component 26 is configured to receive the anchor 24. The second body section 26b includes a rod 27 attached in the first body section 26a of the anchor deployment component 26. The rod 27 extends through a channel formed in an internal wall 23 of the delivery guide 22. In one embodiment an anchor cup 29 is provided at a distal end of the rod 27 to receive and releasably hold a proximal end of anchor 24. The anchor cup 29 holds the anchor 24 with a force, e.g. by a press fit provided by an inner diameter Dcup of the anchor cup 29 being slightly less than an outer diameter D (FIG. 3B) of the anchor. The force is adapted to be sufficient to hold the anchor 24 in place until the anchor 24 is implanted in the tissue, but less than a force required to pull the anchor 24 of out of the anchor cup 29 when the anchor is inserted into a tissue location. Furthermore, a proximal surface, or anchor cup bottom 29a, is provided to push against a proximal end of the anchor 24 and drive the anchor 24 into the tissue. The anchor cup 29 includes sidewalls 29b tapering distally towards an outer surface of the anchor 24 to facilitate insertion into tissue.

A diameter Drod of rod 27 is relatively smaller than diameter Dfirst of the first body section 26a of anchor deployment component 26. The sizing of the rod 27 is selected to accommodate a spring mechanism 28 provided between the anchor deployment component 26 and the delivery guide 22. In one embodiment, the spring mechanism 28 includes a spring 50 attached to the delivery guide 22 and a spring seat 52 provided on the anchor deployment component 26. The spring 50 is attached to the internal wall 23 of the delivery guide 22 and the spring seat 52 is provided at a distal end of the first body section 26a of the anchor deployment component 26. Other attachment positions of the spring and the spring seat are acceptable. For example, in another embodiment, the spring 50 is attached to the distal end of the first body section 26a of the anchor deployment component 26 and the spring seat 54 is provided on a proximal side of the internal wall 23 of the delivery guide 22. The spring 50 and the spring seats 52, 54 are attached to the respective parts 22 or 23. The attachments can be done by any suitable means including, but not restricted to, gluing, welding and casting. In one embodiment, the spring seats 52, 54 include a metal sheet configured to provide stabile support for the compression of the spring 50. The spring 50 is shown in an uncompressed (or unloaded) configuration wherein neither the anchor 24 nor the anchor deployment component 26 extends beyond the distal end 22d of the delivery guide 22.

FIG. 2A illustrates one embodiment of the surgical suture fixation system 20 wherein a distal portion 26b of the anchor deployment component 26 includes a cannula 60. Apart from the cannula 60, the other features shown in FIG. 2A are similar to the described features of FIGS. 1A-1B and have corresponding reference numbers. For illustration purposes, only an outline of the delivery guide 22 is shown in phantom line. The surgical suture fixation system 20 is suited for manual manipulation by a surgeon. The surgical suture fixation system 20 is suited for use with robotic surgical systems where the device 20 is delivered through a laparoscopic port to the tissue location inside the patient.

The system 20 is shown with the spring 50 in an uncompressed state. In one embodiment, a proximal end of cannula 60 is fixed/attached to the first body section 26a of anchor deployment component 26. The anchor 24 and the suture 40 are received in the cannula 60 of anchor deployment component 26 (indicated by dotted line). The cannula 60 includes a pointed distal end 62 and an opening 64 sized to receive a body of the anchor 24. In one embodiment a slot 66 is formed through a wall of the cannula 60. The slot 66 provides an exit for the length of suture 40 when the anchor 24 is loaded in the cannula 60 and also provides passage for at least the eyelet 42 to extend outside of the cannula 60. The anchor deployment component 26 defines a longitudinal extent L between its proximal end 26p and its distal end 26d at a distance from the proximal end 26d. The distance of the longitudinal extent L is in a range of 3-15 inches, such as a longitudinal extent L from 4-12 inches, such as a longitudinal extent L from 5-9 inches, or a longitudinal extent L of about 7 inches.

FIG. 2B is a schematic side view of one embodiment of the surgical suture fixation system 20. The anchor deployment mechanism 26 has been moved in a distal direction indicated by arrow A by engaging the distal end 22d of the delivery guide 22 (outlined in phantom line as in FIG. 2A) against tissue and pushing the proximal end 26p of the anchor deployment component 26 in the distal direction. An outer surface of section 26a of the anchor deployment component 26 includes a criss-cross pattern to provide a no-slip or reduced slip surface for the surgeon. Additionally or alternatively, an outer surface of the delivery guide 22 includes an easily grippable surface.

When the anchor deployment component 26 is pushed in the distal direction, the cannula moves beyond the distal end 22d of the delivery guide 22 and penetrates the tissue.

Movement of the distal end of the primary body 26a toward the internal wall 23 of the delivery guide 22 compresses the spring 50, thus enclosing the compressed spring 50 between the primary body 26a and the internal wall 23. Releasing the compressed spring 50 will eject, or move, the cannula 60 out of the tissue, leaving the anchor 24 in place in the tissue.

In one embodiment the spring mechanism 28 includes a spring holding pin and ratchet device configured to keep the spring in the compressed condition without applying a continued pressure to the first body section 26a. The spring holding device includes a controllable release mechanism for releasing the spring from the compressed state, thereby retracting the cannula 60 from the tissue location. In some applications, the pointed distal end 62 of the cannula 60 is sharp and needle-like and is so configured to enter the periosteum tissue covering a boney surface and glide under the periosteum tissue and over the bone. In this manner, the cannula 60 is configured to deliver the anchor 24 (not shown) between the periosteum tissue and the bone.

FIG. 3A is a perspective view of one embodiment of the anchor 24 and FIG. 3B is an end view of the anchor 24. The anchor 24 includes multiple spines 47 extending from the body 44. In one embodiment, the spines 47 project radially away from a center longitudinal axis A of the body 44, with each spine 47 shaped as a shark fin having a curved leading edge 70 that meets with a curved trailing edge 72 at a point P. The curved leading edge 70 is oriented to diverge away from the pointed leading end 46 of the body 44 to allow the anchor 24 to glide into tissue and prevent the anchor from pulling out of the tissue. Although three spines 47 and one eyelet 42 are illustrated, the anchor 24 is also suitably provided with a single spine 47 and one eyelet 42. The anchor 24 is also suitably provided with more than three spines 47.

The eyelet 42 projects radially away from the center longitudinal axis A of the body 44 and as such is also configured to engage with tissue. For example, the eyelet 42 is provided with a height HE that is substantially equal to the height of the spines 47 (the distance that the point P is away from the center axis A). The eyelet has a width substantially equal to the width W of the spine 47.

The body 44 of the anchor 24 is substantially circular in lateral cross-section (FIG. 3B). The anchor 24 is configured to slide in an entry direction through the tissue, and is shaped to prevent withdrawal of the anchor 24 in the direction that is opposite of the entry direction, i.e. a proximal direction. The curved leading edge 70 of the shark fin shape of the spines 47 facilitate the easy sliding of the anchor 24 through the tissue in the entry direction, and the curved trailing edge 72 of the spines 47 configure the anchor to resist being pulled out of the tissue in the direction that is opposite of the entry direction. In one embodiment, the body 44 of the anchor 24 has a diameter D, and the spine 34 has a width W that is less than about 25% of the diameter D (FIG. 3B).

FIG. 3C is a perspective view of one embodiment of an anchor 24' provided with an eyelet 42'that is disposed on the center longitudinal axis A of the body 44. The spines 47 of the anchor 24' are provided to engage with tissue, and the eyelet 42' is streamlined to follow the body 44 into the tissue channel that is formed when the anchor 24' is driven into the tissue by the anchor deployment component 26.

Figure 4:
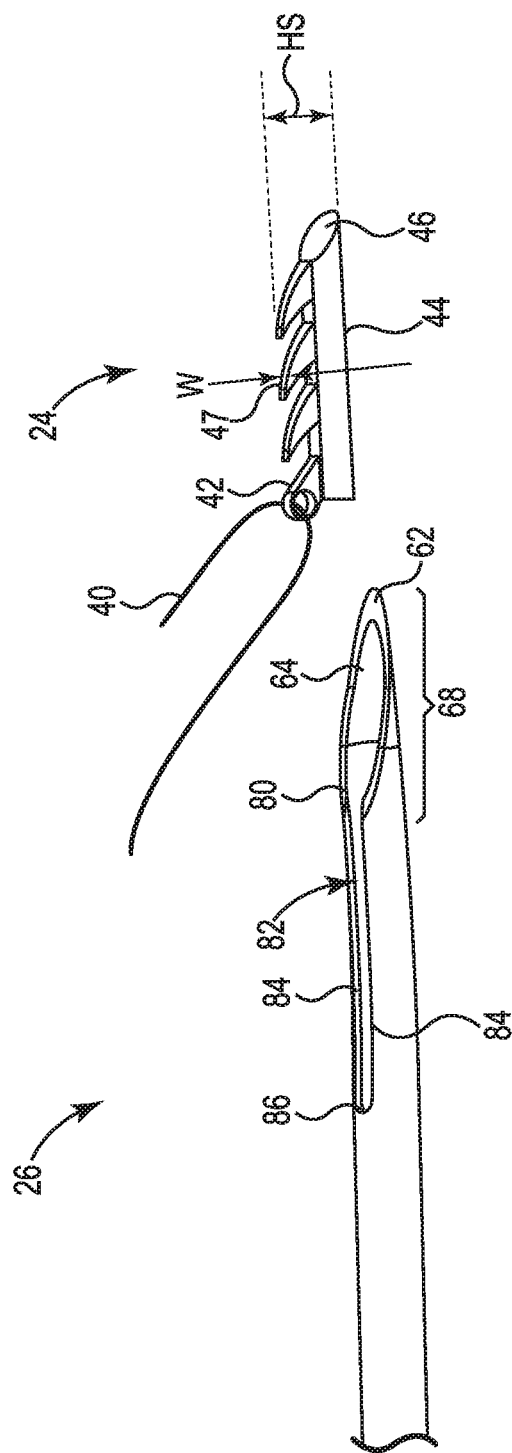
FIG. 4 is a perspective view of an anchor outside of the anchor deployment component illustrated in FIG. 2A.

FIG. 4 is a perspective view of the anchor 24 positioned for insertion into the cannula 60 of the anchor deployment component 26 and FIG. 5 is a perspective view of the anchor 24 inserted into the cannula 60. The body 44 of the anchor 24 is sized to slide into the opening 64 (also called a lumen 64) of the cannula 60 with the spine 47 projecting out of the cannula 60. With reference to FIG. 4, the inside diameter of the lumen 64 of the cannula 60 provides a cannula diameter CD, and the spine 47 has a height HS that is greater than the cannula diameter CD. The height HS of the spine 47 is at least 5% greater than the cannula diameter CD. For example, the height HS of the spine 47 is in the range of 5-100% greater than the cannula diameter CD.

It is acceptable for the height HE (FIG. 3A) of the eyelet 42 to be equal to the height HS of the spine 47. It is also acceptable for the height HE (FIG. 3A) of the eyelet 42 to be different from and not equal to the height HS of the spine 47.

The cannula 60 includes a tapered distal end portion 68 that tapers to the pointed distal end 62, where the tapered distal end portion 68 provides the cannula 60 with a needle-like point adapted for insertion through tissue.

The cannula 60 has a wall 80 that forms or defines the lumen 64 and a slot 82 formed through the wall 80. The slot 82 is proximal of the tapered distal end portion 68 and extends through the wall 80 to communicate with the lumen 64. The slot 82 includes a pair of opposed longitudinal side edges 84 that extend from a proximal lateral edge 86 in a distal direction to the distal end portion 68. The width of the slot between the longitudinal side edges 84 is sized to receive the width W of the spines 47. The cannula diameter CD is sized to receive the diameter D (FIG. 3B) of the body 44 of the anchor 24.

With reference to FIG. 5, when the anchor 24 is loaded into the cannula 60, the pointed leading end 46 of the body 44 is located proximal of the pointed distal end 62 of the cannula 40, and the spines 47 and the eyelet 42 extend outside of the cannula 60 and are positioned to engage with tissue during implantation of the anchor 24. The proximal lateral edge 86 of the slot 82 is positioned to push against the eyelet 42 and drive the anchor 24 into the tissue. The opposed longitudinal side edges 84 of the slot 82 provide a stanchion that restrains the spines 47 and prevents the anchor 24 from rotating relative to the cannula 60. The spines 47 and the eyelet 42 slide in a longitudinal direction relative to the slot 82 to allow the cannula 60 to be removed from the tissue while leaving the anchor 24 implanted.

Suitable materials for fabricating the anchor 24 include plastics, or metal, or sintered material. One suitable material for fabricating the anchor 24 is polypropylene. Another suitable material for fabricating the anchor 24 is a bioabsorbable polymer that configures the anchor 24 to be absorbed into the body over a period of several weeks.

Suitable materials for fabricating the length of suture 40 include bio-inert components that do not bioabsorb, or bioabsorbable components that are configured to be absorbed or resorbed by the body. One suitable material for fabricating the length of suture 40 is polypropylene. Other suitable materials for fabricating the length of suture 40 include dissolvable sutures available from Ethicon™, a J&J Company located in Somerville, N.J., and include Monocryl™ (polyglycaprone 25) sutures, coated Vicryl™ (polyglactin 910) sutures, Ethicon Plus™ Sutures, or polydioxanone sutures as examples.

Suitable materials for fabricating the cannula 60 and the anchor deployment component 26 include plastics or metal. One suitable material for fabricating the cannula 60 is stainless steel. One suitable material for fabricating the anchor deployment component is Nitinol, a metal alloy of nickel and titanium. Other suitable materials are acceptable.

Figure 6A:
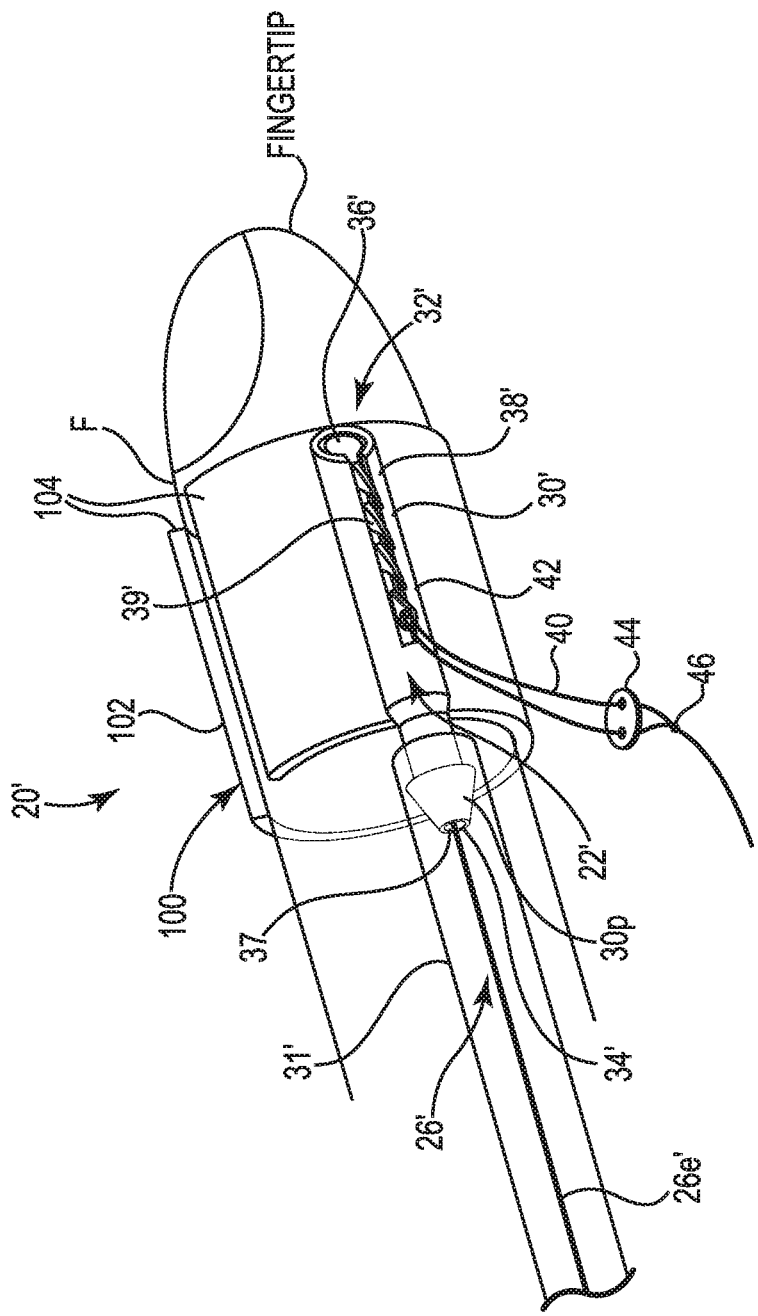
FIG. 6A is a perspective view of one embodiment of a surgical suture fixation system including a finger housing.
Figure 6B:
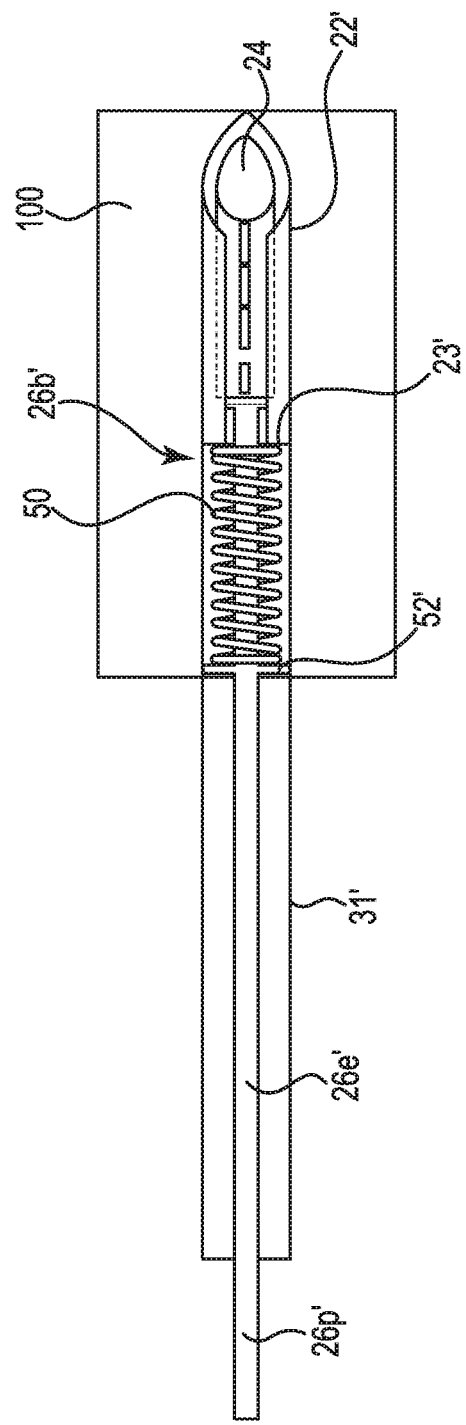
FIG. 6B is a partial cross-sectional view of one embodiment of a surgical suture fixation system including the finger housing illustrated in FIG. 6A.

FIG. 6A is a perspective view and FIG. 6B a partial cross-sectional view of one embodiment of a surgical suture fixation system 20' including a delivery guide 22', an anchor 24, a movable anchor deployment component 26' and a spring mechanism 28. Surgical suture fixation system 20' also includes a finger housing 100 coupled to the delivery guide 22'.

The delivery guide 22' includes a conduit 30' having a distal end 32' and a proximal end 34'. The conduit 30' of the delivery guide 22' includes openings 36' and 37' in the distal and proximal ends 32', 34' respectively, and a channel 38' formed through a sidewall 39' for some of the length of the conduit 30'. In one embodiment, the channel 38' extends from the distal end 32' of the conduit 30' and at least a part of the distance to the proximal end 34' of the conduit 30'. In one embodiment, the openings 36' and 37' in the distal and proximal ends 32', 34' are sized to provide passage for the movable anchor deployment component 26' to move proximally and distally through the openings 36', 37'.

In one embodiment, the movable anchor deployment component 26' includes an elongated stick element 26e' extending between a proximal end 26p' and a distal end 26d', the distal end 26d' engaging into the delivery guide 22' through the opening 37' in the conduit 30'. In one embodiment, the distal end 26d' of the anchor deployment component 26'. The stick element 26e' extends from proximal end 26p' into engagement with the delivery guide 22' through opening 37' in the proximal end 34' of the conduit 30' where its distal end 26d' receives anchor 24. In one embodiment, the stick element 26e' is a rigid wire like component having a significantly higher resistance to bending than a tubing 31' enclosing the element 26e'. In one embodiment, the tubing 31' is configured to be attached to the delivery guide 22' around a proximal portion 30p' of the conduit 30'. In some configurations, the proximal portion 30p' includes a proximally tapering section and defines a ledge a distal end of the tapering section, the proximal portion 30p' configured to receive and hold one end of the tubing 31'. In another embodiment, the tubing 31' and the conduit 30' are monolithically associated.

In some applications, conduit 30' of the delivery guide 22' and tubing 31' in total encloses between 10-100% of the longitudinal extent L of the anchor deployment component 26'. For example, the proximal end 26p' of the anchor deployment component 26' is configured to extend "out of the tubing 31" to provide for manual manipulation of the proximal end 26p' (FIG. 6B).

In one embodiment, the anchor 24 has a length of suture 40 attached to it through an eyelet 42 provided on the anchor 24. The anchor 24 is received by the movable anchor deployment component 26' located in the conduit 30' of the delivery guide 22' to be in a position ready for insertion into tissue. A length of suture 40' is shown exiting through the channel 38' of the delivery guide 22. In one embodiment, the length of suture 40 includes an engagement slider 44 and a slip knot 46.

The finger housing 100 is attachable to (or on) a finger F of a person, such as a practitioner. The finger housing 100 is configured to leave at least a distal tip of the finger F available to palpate tissue and identify a desired (or target) tissue location. In one embodiment, the finger housing 100 includes a through-going opening 102 defined by a pair of opposing longitudinal edges 104. The opening provides flexibility to the finger housing including accommodation of different finger sizes. In one embodiment, the finger housing 100 is coupled to the delivery guide 22' as a separate component attached by gluing or otherwise mechanically connected to the delivery guide. In another embodiment the finger housing 100 is monolithically associated with the delivery guide 22'. For example, the finger housing 100 and the delivery guide 22' can be integrally cast or injection molded. The finger housing 100 and the delivery guide 22' are coupled to each other adjacent a distal portion of the anchor deployment mechanism 26'.

A spring mechanism 28' is provided between the anchor deployment component 26' and the delivery guide 22' as it is schematically illustrated in FIG. 6B. In one embodiment, the spring mechanism 28' includes a spring 50' attached to an internal wall 23' of the delivery guide 22' and a spring seat 52' provided on the anchor deployment component 26'. The anchor 24 is shown inserted in the distal end of a second body section 26b' of the movable anchor deployment component 26'. Second body section 26b' is configured as an elongated section of stick element 26e'. The elongate section extends through an opening in an internal wall 23' of the delivery guide 22'. In one embodiment an anchor cup 29' is provided at a distal end of the elongated section of stick element 26e' to receive and releasably hold a proximal end of an anchor 24 inserted therein. Anchor 24 includes an anchor of one the types illustrated in FIG. 3A-3C and is provided and received in the anchor cup 29'. In one embodiment, the eyelet 42 extends through the channel 38' in the sidewall 39' of the conduit 30' while fins 47 of the anchor 24 extend at least partly through the channel 38' and are just visible in FIG. 6. For further description on the features of FIG. 6B and their interactions, please see the specification's description of the corresponding features of FIG. 1B.

FIG. 7A is a perspective view of one embodiment of the surgical suture fixation system 20' including finger housing 100 with the distal end 26d' of the anchor deployment component 26' including a cannula 60' for receiving an anchor 24. In one embodiment, the cannula 60' is configured as an elongated section of the anchor deployment component 26'. In another embodiment, the cannula 60' is provided as a separate element coupled to the distal end 26d' of the anchor deployment component 26'.

The cannula 60' includes a tapered distal end portion 68' that tapers to the pointed distal end 62', where the tapered distal end portion 68' provides the cannula 60' with a needle-like point adapted for insertion through tissue. The cannula 60' also includes a slot 66'. For further description on cannula 60', please see the specification's description of the corresponding features of FIG. 4.

The anchor 24 includes an anchor of the types illustrated in FIG. 3A-3C and is provided and received in the cannula 60'. In one embodiment, the eyelet 42 and the fins 47 only extend through the slot 66' in the cannula 60', but not through the channel 38'. In another embodiment, eyelet 42 and fins 47 of the anchor 24 extend through both the slot 66' in the cannula 60' and at least partly through channel 38' of the conduit 30' of the delivery guide 22' (not illustrated). FIG. 7 also illustrates the length of suture 40 exiting through the slot 66' and the channel 38' and having engagement slider 44 and slip knot 46 provided thereon externally of the delivery guide 22'. The anchor 24 is sized and shaped to go into soft tissue and slide along bone, such as, but not limited to, going into the periosteum tissue along the pubic bone.

Figure 7B:
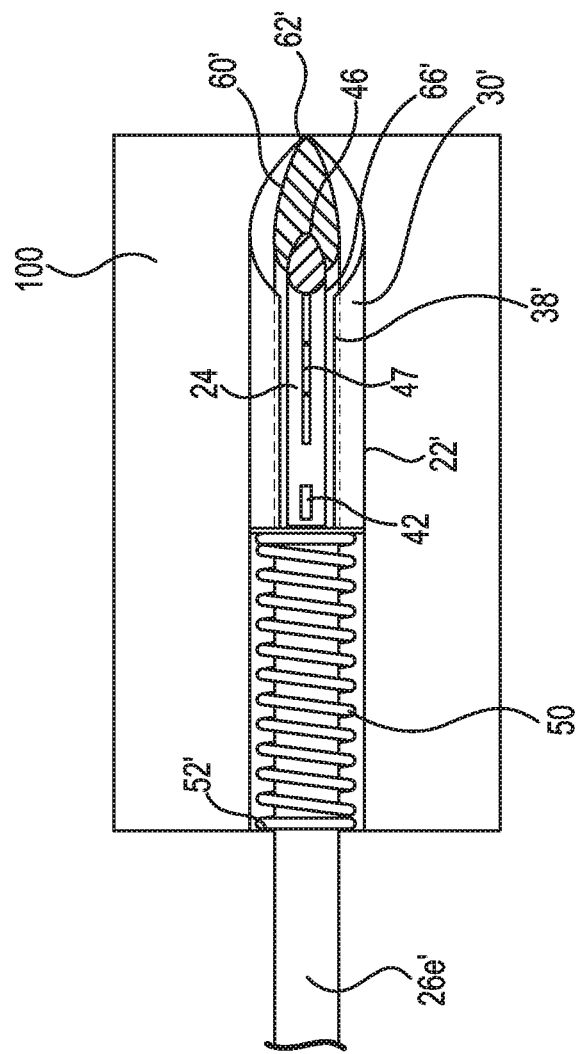
FIG. 7B is a partial cross-sectional view of the surgical suture fixation system illustrated in FIG. 7A.

FIG. 7B is a schematic and partial cross-sectional view of a distal portion of the surgical suture fixation system 20' illustrated in FIG. 7A. The spring 50 is provided between the delivery guide 22' and a spring seat 52' on the anchor deployment component 26'. The spring 50' is shown in an uncompressed state and the cannula 60' including the anchor 24 has not moved distally out of the conduit 30' of the delivery guide 22'. The anchor 24 including pointed leading end 46 positioned proximal to pointed distal end 62' of the cannula 60', eyelet 42 and fins 47, is partly visible through both channel 38' of the conduit 30' and slot 66' of the cannula 60'. As mentioned above, the eyelet 42 and the fins 47 extend through at least the slot 66' of the cannula 60' and in embodiments also through the channel 38' in the conduit 30'. Eyelet 42 and fins 47 extend radially away from central axis A (FIG. 3A) of the cannula 60', i.e. out of the plane of the paper towards the reader.

Figure 8:
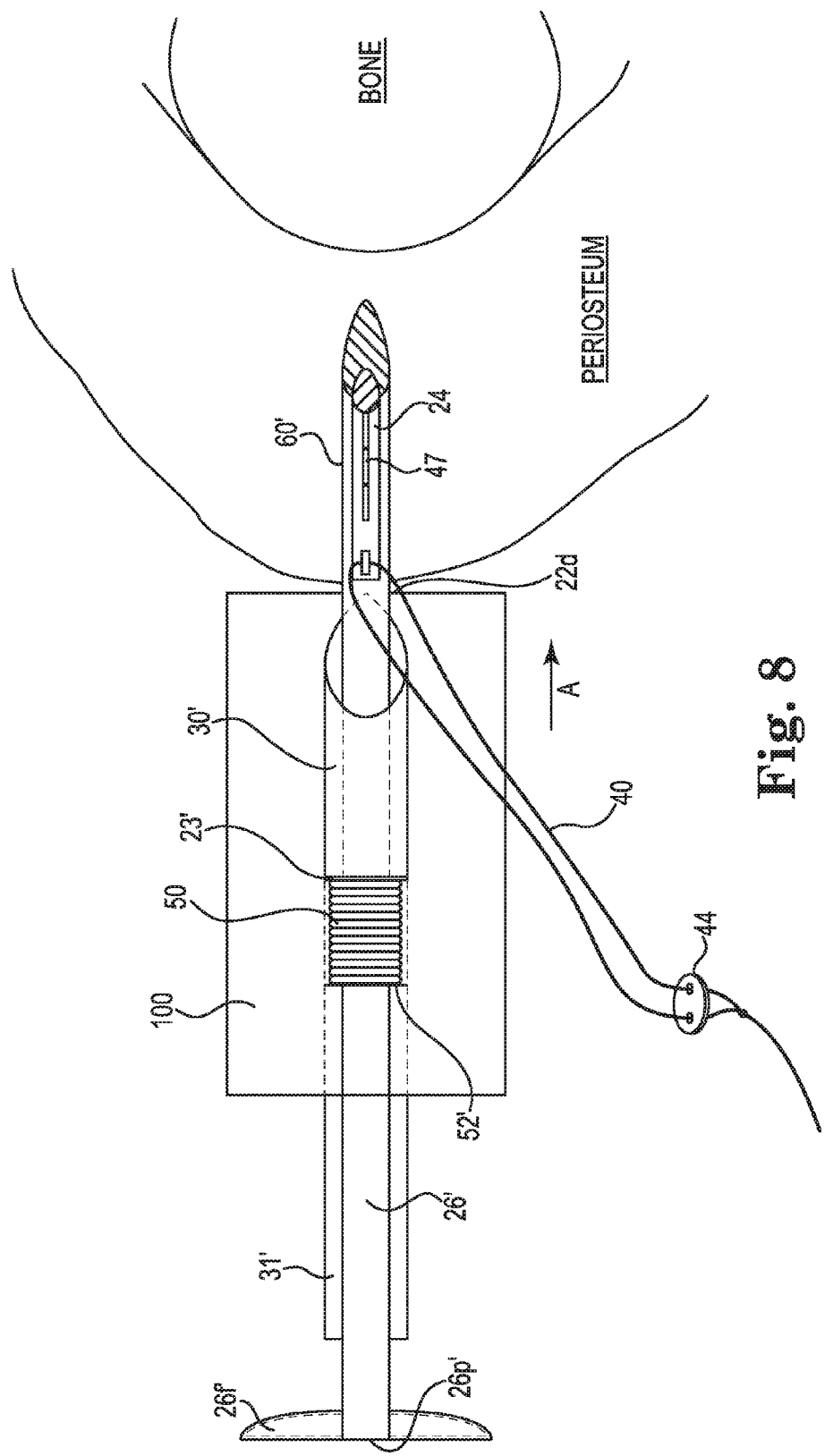
FIG. 8 is a side view of one embodiment of a surgical suture fixation system showing the anchor deployment component inserted into a tissue location.

FIG. 8 is a schematic and partial cross-sectional view of the distal portion of the surgical suture fixation system 20' employed to place the anchor 24 into tissue. The anchor deployment mechanism 26' has been moved in a distal direction indicated by arrow A into a tissue location by pushing the proximal end 26p' of the anchor deployment component 26' out of tubing 31'. The anchor deployment component 26' includes a grip 26f' or a flange 26f' near the proximal end 26p'. By moving the anchor deployment component 26' distally, the cannula 60' extends out and beyond the distal end 22d' of the delivery guide 22' to penetrate and enter into the tissue location. As described in more detail with reference to FIGS. 3A-3C, the curved leading edge 70 of the shark fin shape of the spines 47 of the anchor 24 facilitate easy sliding of the anchor 24 through the tissue in the entry direction, and the curved trailing edge 72 of the spines 47 configure the anchor 24 to resist being pulled out of the tissue in the direction that is opposite of the entry direction. The distal movement of the anchor deployment component 26' compresses the spring 50 because the spring seat 52' is coupled to the anchor deployment component 26' and thus also moves in the distal direction. This movement encloses the compressed spring 50 between the spring seat 52' and the internal wall 23'.

Figure 9:
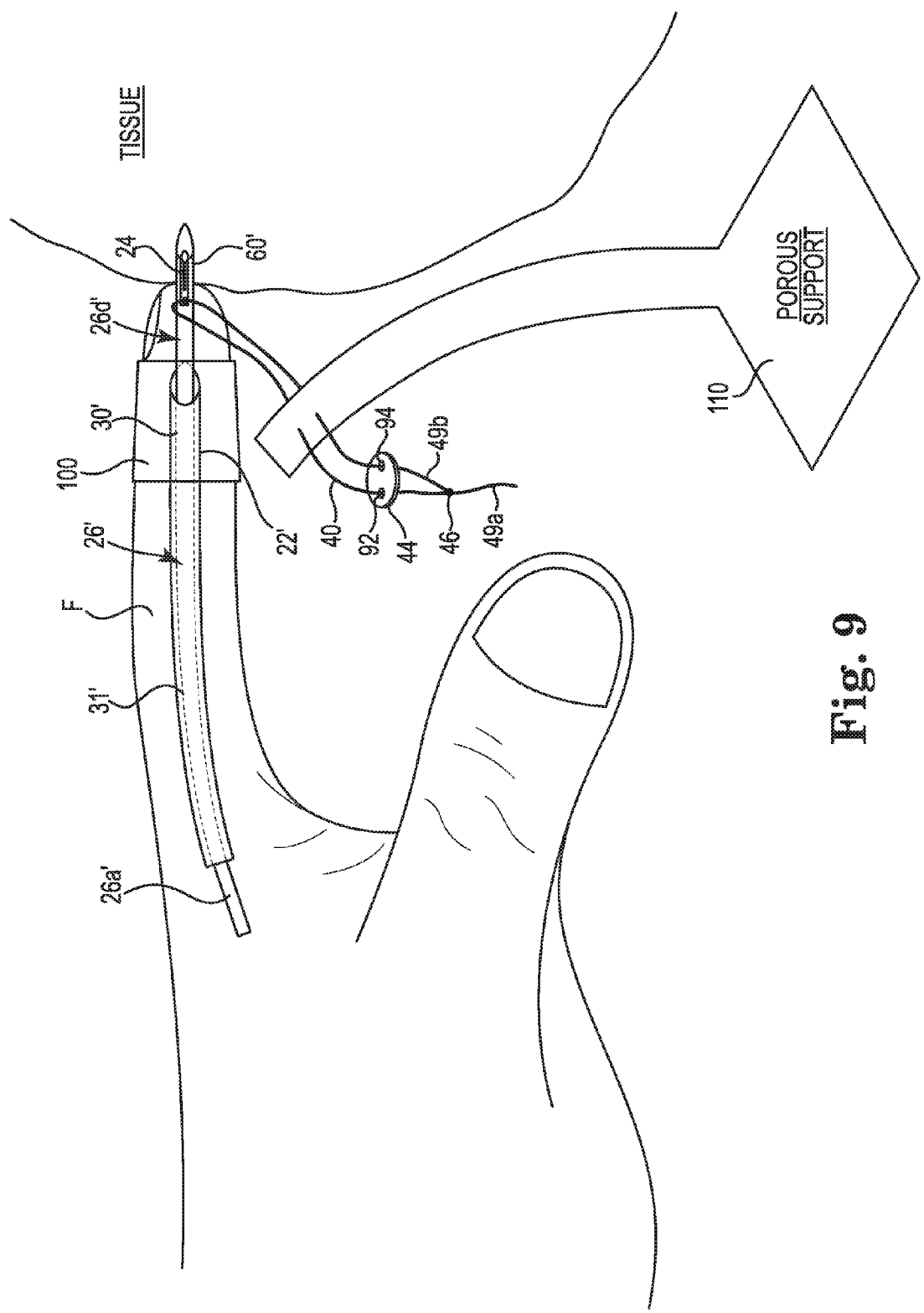
FIG. 9 is a perspective view of one embodiment of a surgical suture fixation system including a finger housing applied on a user's finger.

FIG. 9 is a perspective view of one embodiment of the system 20' including the finger housing 100. The finger housing 100 is mounted or applied to a finger F of a practitioner. A distal tip of the practitioner's finger F is shown contacting a tissue location including a location on the periosteum tissue covering the pubic bone PB, on the sacrospinous ligament or on the arcus tendenius ligament. In one embodiment, the anchor deployment component 26' includes a first body section 26a' at least partly enclosed in tubing 31', the tubing 31' including a material and dimensions with less resistance to bending than the anchor deployment component 26'. The distal end 26d' of the anchor deployment component 26' includes cannula 60' and is shown in a position in which it has been moved distally out of the conduit 30' of the delivery guide 22' and into a tissue location. Anchor 24 is shown in its position received in the cannula 60'. The system 20' is in a position where the anchor 24 is delivered to a desired tissue location, and where the anchor deployment component 26' has not yet been moved proximally out of the tissue. In this position, the spring 50 of the spring mechanism (FIG. 8B) is in a compressed state. In one embodiment, when the anchor deployment component 26' is moved in the proximal direction, the spring 50 is released from its compressed state and the cannula 60' is withdrawn from the tissue location leaving the anchor 24 fastened in the tissue location. The release of the spring 50 of the spring mechanism causes the cannula 60' to eject from the tissue location in a quick movement with little or no physical force required by the surgeon to move the cannula in the proximal direction. This makes the retraction of the cannula easier and controls the retraction path of the cannula back through the tissue canal established by the initial insertion of the cannula. In some applications, the proximal end 26p' of the anchor deployment component 26' is provided at a distance from the distal end 26d' (FIG. 2A). This allows manual engagement of the proximal end 26p' to take place in a position clear of other tissue, such as outside a patient's body. FIG. 9 also schematically illustrates a porous support material 110 to be implanted in a patient, a part of which is engaged by the length of suture being 40 fastened in the tissue location by anchor 24.

One embodiment of the system 20' illustrated in FIG. 9 includes an engagement slider 44 that is attached to the suture 40, where the engagement slider 44 is configured to slide along the suture 40 and direct the support 110 into the patient's body and against the tissue. In one embodiment, the engagement slider 44 has a first orifice 92 and a second orifice 94. An anchor 24 is engaged with tissue, e.g. the periosteum tissue of the pubic bone or a ligament, and a first end 49a of the suture 40 extends from the anchor 24 through the first orifice 92, and a second end 49b of the suture 40 extends through the second orifice 94 and defines a slip knot 46 together with the first end 49a of the suture. The slip knot 46 (or alternatively another termination device) is provided to tie the suture 40 against the engagement slider 44 after the engagement slider 44 and the support 110 has been delivered to the pubic bone or ligament. The engagement slider 44 is located between the anchor 24 and the slip knot 46. The engagement slider 44 slides along the suture 40 and is operable to push or otherwise deliver the support 110 against the pubic bone or ligament.

Suitable materials for fabricating the support 110 include porous materials that allow tissue ingrowth throughout the support structure to anchor the support 110 in the body after implantation and healing. Suitable such porous materials include autograft material (the patient's own tissue), allograft material (tissue from a cadaver), xenograft material (tissue from another species), or synthetic materials such as woven fabrics, meshes, nonwoven fabrics, meshes, fibrillated fibers, or spun and fibrillated fibers that are provided with voids (pores) configured to allow tissue ingrowth into the support 110. The pores are generally larger, on average, than 75 µm.

Suitable materials for fabricating the finger housing 100 include plastics or metal. One suitable material for fabricating the finger housing 100 is polyethylene. Other suitable materials are acceptable.

Suitable materials for fabricating the anchor deployment component 26' include plastics or metal. One suitable material for fabricating the anchor deployment component 26' is Nitinol, a metal alloy of nickel and titanium. Other suitable materials are acceptable.

Suitable materials for fabricating the tubing 31' include plastics or metal. One suitable material for fabricating the tubing 31' is polyurethane. Other suitable materials are acceptable.

Suitable materials for fabricating the engagement slider 44 include plastics or metal. One suitable material for fabricating the engagement slider 44 includes polypropylene. Another suitable material for fabricating the engagement slider 44 includes stainless steel. In one embodiment, the engagement slider 44 is fabricated to be bioabsorbable.

In an aspect, the application relates to a method of fixing surgical suture to tissue.

Figure 10:
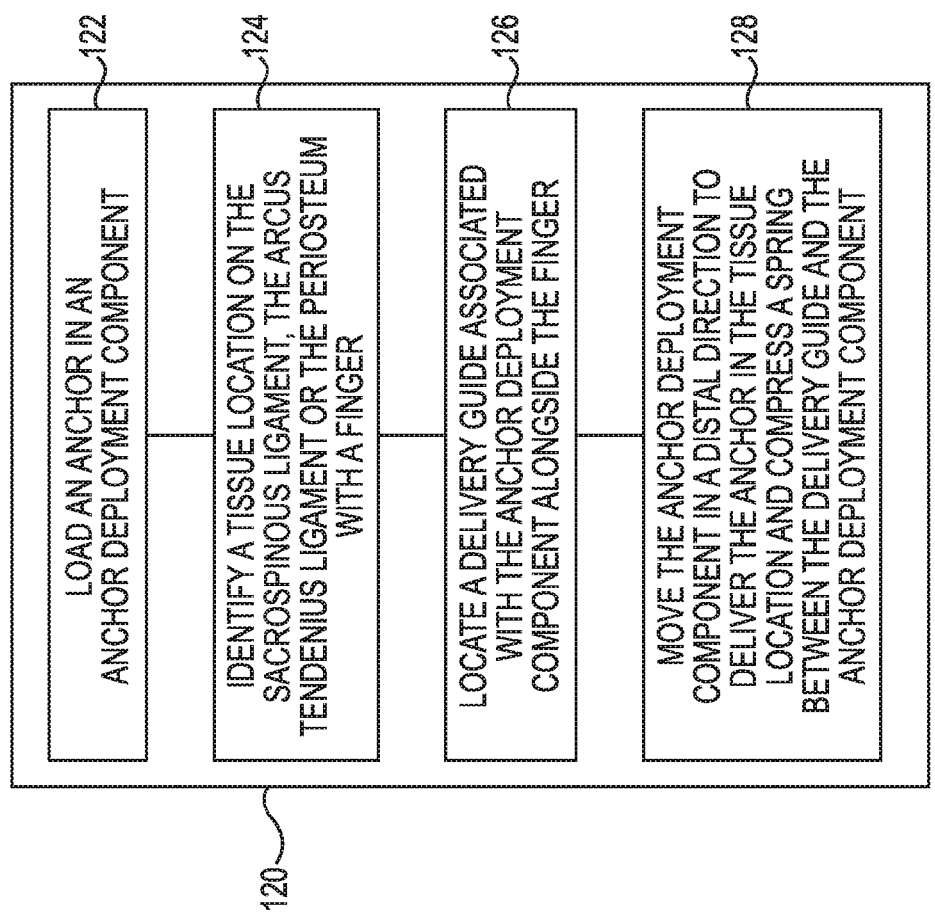
FIG. 10 is a block diagram of one embodiment of a method of fixing surgical suture to tissue.

FIG. 10 is a block diagram 120 of one embodiment of a method of fixing surgical suture to tissue. The method includes at 122 loading an anchor having a length of suture attached thereto in an anchor deployment component 26, 26'. The method includes at 124 identifying a tissue location on the sacrospinous ligament, the arcus tendenius ligament or the periosteum with a finger. The method of fixing surgical suture to tissue includes at 126 locating a delivery guide 22, 22' associated with the anchor deployment component 26, 26' alongside the finger. The method includes at 128 moving the anchor deployment component 26, 26' in a distal direction to deliver the anchor 24 in the tissue location and compressing a spring 50 between the delivery guide 22, 22' and the anchor deployment component 26, 26'.

With additional reference to FIGS. 2A, 2B, 8 and 9, a surgical suture fixation system 20, 20' including a length of surgical suture 40 is provided for attaching the suture to a desired tissue location in a patient in an intracorporeal suturing procedure. The length of suture is attached to the anchor 24. The suture is configured to extend through a support material 110, the support material 110 including a porous support or mesh type support material for supporting internal organs or tissues. The anchor 24 is useful for fixating the support material 110 within the patient's body. The system 20, 20' is sized to be able to deploy the anchor 24 through a single incision and into the periosteum tissue that covers the pubic bone or to a ligament, particularly including the sacrospinous and arcus tendenius ligaments.

EXAMPLE

The following example illustrates, with particular reference to FIGS. 2A-2B and FIGS. 8 and 9, the fixation of surgical suture using the system described above.

The patient is prepared for the relevant type of surgery, such as, but not limited to, sacropolpopexy surgery in a female patient. The patient is positioned on a surgical operating table in a lithotomy, or modified lithotomy position, and is anesthetized.

The surgeon makes an incision in the pelvic region of the patient. One acceptable incision approach is a single incision approach including the formation of a single (exactly one) incision in the anterior wall of the vagina (e.g., an upper wall of the vagina with the patient in the lithotomy position). Tissue is dissected lateral and distal the incision to access the supporting ligaments and other tissue in the pelvis.

The anchor 24 is driven through the material of the support 110 prior to or subsequent to loading the anchor 24 in the anchor deployment component 26. The fixation device 44 is arranged outside of the anchor deployment component 26 and the delivery guide 22. The suture is attached to the anchor.

The delivery guide 22 is placed near, or alongside, the distal tip of a finger of the surgeon. The surgeon inserts the finger and the distal portion of the surgical suture fixation system through the incision to reach a tissue location inside the pelvic region of the patient. The surgeon palpates the tissue with the distal tip of the finger to identify the desired tissue location for placement of the anchor 24. Typically, the surgeon palpates for this location since it is not visible through the incision.

The proximal end of the anchor deployment component 26 is then pushed in the distal direction by the thumb of the hand that has palpated the tissue location or by the other hand, depending upon the surgeon's preference. The distally-directed force operates to translate and insert the cannula 60 of the distal portion of the anchor deployment component 26 (that has been loaded with the anchor 24) into the tissue location. Pushing the anchor deployment component 26 in the distal direction compresses the spring 50 of the spring mechanism of the system.

The anchor deployment component has a length such that its proximal end is located visibly outside the incision in the patient's body and is engaged to release the compressed spring. Releasing the spring from its compressed state forces the anchor deployment component to move in the proximal direction, which ejects and retracts the cannula from the tissue location. As a consequence, the anchor is fastened in the tissue location while the surgeon still has her/his finger tip located at the tissue location. The fixation device 44 is slid along the suture 40 and directs the support 110 into the patient's body and against the tissue.

Some surgical suture fixation systems do not allow the practitioner to deliver the suture without having to move the tip of the palpating finger located on the identified tissue location.

The surgical suture fixation system presented herein provides a system that gives the surgeon the option to palpate and identify a desired tissue location while simultaneously providing the anchor and suture in the desired tissue location without having to move her/his finger or apply a separate device to fasten the suture to the tissue. This makes it possible to load and insert the anchor attached with the suture, the support and the fixation device into the identified tissue location as part of the same procedure thereby avoiding the need to re-identify a tissue location and to use more than one surgical tool or device to fasten the suture to the tissue. The surgical suture fixation system provides for intracorporeal suturing with the suture line conveniently available outside of the patient's body.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of medical devices as discussed herein. Therefore, it is intended that this invention be limited only by the claims and the equivalents thereof.

What is claimed is:

1. A method of fixing surgical suture to tissue, the method comprising:
providing a suture fixation system including: a delivery guide; an anchor deployment component having a cannula movable within the delivery guide; and a spring positioned around a portion of the cannula and retained between a first spring seat of the anchor deployment component and a second spring seat formed inside of the delivery guide;
loading an anchor into the cannula by loading the anchor into a conduit of the deliver guide, with the conduit having an opening in a distal end and a channel formed in a sidewall of the conduit, with a portion of the anchor extending out of the conduit and through the channel;
locating a fixation device outside of the delivery guide, with the anchor and the fixation device attached by a suture; and
moving the anchor deployment component in a distal direction and moving the cannula through an opening in a distal end of the delivery guide and into the tissue, pushing the anchor out of the delivery guide and into the tissue, and delivering the anchor into the tissue.

2. The method according to claim 1, further comprising:
engaging a support material with the suture and locating the support material between the anchor and the fixation device.

3. The method according to claim 1, further comprising:
engaging a support material with the suture and locating the support material between the anchor and the fixation device; and
sliding the fixation device along the suture and forcing the support material into contact with the tissue.

4. The method according to claim 1, further comprising:
engaging a support material with the suture and locating the support material between the anchor and the fixation device; and
delivering the support material along the suture from outside of a patient to the anchor located inside the patient.

5. The method according to claim 1, further comprising:
engaging a porous support material with the suture; and
delivering the porous support material along the suture from outside of a patient to the anchor located inside the patient.

6. The method according to claim 1, further comprising:
engaging a support material with the suture;
delivering the support material along the suture from outside of a patient to the anchor located inside the patient; and
supporting an organ of the patient with the support material.

7. The method according to claim 1, further comprising:
creating an incision in a vagina of a patient;
inserting the delivery guide and the anchor into the incision;
engaging a support material with the suture;
delivering the support material along the suture through the incision and into the patient; and
supporting an organ of the patient with the support material.

8. The method according to claim 1, further comprising:
creating exactly one incision in a vagina of a patient;
inserting the delivery guide and the anchor into the incision;
engaging a support material with the suture;
delivering the support material along the suture through the incision and into the patient; and
supporting an organ of the patient with the support material.

9. The method according to claim 1, comprising an eyelet of the anchor extending out of the conduit and through the channel and the suture engaged with the eyelet of the anchor.

10. The method according to claim 1, comprising:
loading the anchor into the conduit of the delivery guide, with the anchor having a body including a pointed leading end that is configured to pierce the tissue, a spine projecting radially away from the body and having a width and a height configured to allow the spine to engage with the tissue, and an eyelet attached to a trailing end of the body; and
projecting the eyelet of the anchor through the sidewall of the conduit.

11. The method according to claim 1, comprising loading the anchor into the conduit of the delivery guide, with the anchor having a body including a pointed leading end that is configured to pierce the tissue and a spine projecting radially away from the body, with the spine providing the anchor with a plurality of teeth.

12. The method according to claim 1, wherein delivering the anchor into the tissue comprises:
retracting the cannula in a proximal direction and into the delivery guide and leaving the anchor in the tissue.

13. The method according to claim 1, further comprising:
compressing the spring between the first spring seat of the anchor deployment component and the second spring seat and moving the anchor deployment component relative to the delivery guide.

14. The method according to claim 1, further comprising:
placing the delivery guide against the tissue;
moving the anchor deployment component in a distal direction relative to the delivery guide;
pushing the cannula and the anchor out of the delivery guide and into the tissue; and
retracting the cannula into the delivery guide and leaving the anchor in the tissue.

15. A method of fixing surgical suture to tissue and supporting an organ in a patient, the method comprising:
creating an incision in a vagina of a patient;
loading an anchor into a cannula and retaining the cannula in a delivery guide;
locating a fixation device outside of the delivery guide, with the anchor and the fixation device attached by a suture;
engaging a porous support material with the suture;
providing an anchor deployment component coupled with the delivery guide and located proximal to the anchor, with a spring mechanism located between a first spring seat on a distal portion of the anchor deployment component and a second spring seat inside of the delivery guide;
inserting the delivery guide and the anchor into the incision;
moving the anchor deployment component in a distal direction through the delivery guide, compressing the spring mechanism between the first spring seat and the second spring seat, pushing the anchor and the cannula in a distal direction out of the delivery guide, retracting cannula in a proximal direction into the delivery guide, and delivering the anchor into tissue;

delivering the support material along the suture through the incision and into the patient;

sliding the fixation device along the suture and fixating the support material relative to the tissue with the fixation device; and supporting a prolapsed organ of the patient with the support material.

16. The method of claim 15, comprising delivering the anchor into periosteum tissue.

\* \* \* \* \*